United States Patent
Trail et al.

(10) Patent No.: US 10,268,290 B2
(45) Date of Patent: *Apr. 23, 2019

(54) EYE TRACKING USING STRUCTURED LIGHT

(71) Applicant: Facebook Technologies, LLC, Menlo Park, CA (US)

(72) Inventors: Nicholas Daniel Trail, Bothell, WA (US); Robert Dale Cavin, Kirkland, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/965,072

(22) Filed: Apr. 27, 2018

(65) Prior Publication Data

US 2018/0246590 A1    Aug. 30, 2018

Related U.S. Application Data

(63) Continuation of application No. 15/335,634, filed on Oct. 27, 2016, now Pat. No. 9,983,709.

(Continued)

(51) Int. Cl.
*G02B 27/00* (2006.01)
*G06F 3/041* (2006.01)
(Continued)

(52) U.S. Cl.
CPC .......... *G06F 3/041* (2013.01); *G01B 11/2513* (2013.01); *G02B 27/0093* (2013.01);
(Continued)

(58) Field of Classification Search
CPC ................................................ G02B 27/0093
See application file for complete search history.

(56) References Cited

U.S. PATENT DOCUMENTS

| 2006/0210111 A1 | 9/2006 | Cleveland et al. |
| 2007/0183293 A1 | 8/2007 | Murata et al. |

(Continued)

FOREIGN PATENT DOCUMENTS

| JP | 3298081 B2 | 7/2002 |
| JP | 2014-219621 A | 11/2014 |

(Continued)

OTHER PUBLICATIONS

PCT International Search Report and Written Opinion, PCT Application No. PCT/US2017/012346, Mar. 30, 2017, 13 pages.

(Continued)

*Primary Examiner* — Ryan R Yang
(74) *Attorney, Agent, or Firm* — Fenwick & West LLP

(57) ABSTRACT

Disclosed is a system and method for tracking a user's eye using structured light. The structured light system is calibrated by training a model of surface of the user's eye. A structured light emitter projects a structured light pattern (e.g., infrared structured light) onto a portion of the surface of the eye. From the viewpoint of a camera, the illumination pattern appears distorted. Based on the distortion of the illumination pattern in the captured image, the eye tracking system can determine the shape of the portion of the user's eye that the structured light is incident upon. By comparing the determined shape of the portion of the user's eye to the model, the orientation of the eye may be determined. The eye tracking system or elements thereof may be part of a head-mounted display, e.g., as part of a virtual reality system.

20 Claims, 6 Drawing Sheets

Related U.S. Application Data

(60) Provisional application No. 62/249,852, filed on Nov. 2, 2015.

(51) Int. Cl.

| | | |
|---|---|---|
| *G06K 9/00* | (2006.01) | |
| *G06T 19/00* | (2011.01) | |
| *G01B 11/25* | (2006.01) | |
| *G06K 9/20* | (2006.01) | |
| *G02B 27/01* | (2006.01) | |
| *G06T 7/70* | (2017.01) | |

(52) U.S. Cl.
CPC ....... *G02B 27/0172* (2013.01); *G06K 9/0061* (2013.01); *G06K 9/00604* (2013.01); *G06K 9/00617* (2013.01); *G06K 9/2036* (2013.01); *G06T 7/70* (2017.01); *G06T 19/006* (2013.01)

(56) References Cited

U.S. PATENT DOCUMENTS

| | | |
|---|---|---|
| 2013/0050070 A1 | 2/2013 | Lewis et al. |
| 2013/0176533 A1 | 7/2013 | Raffle et al. |
| 2013/0241805 A1 | 9/2013 | Gomez |
| 2014/0092139 A1 | 4/2014 | Sullivan et al. |
| 2014/0153102 A1 | 6/2014 | Chang |
| 2014/0211193 A1 | 7/2014 | Bloom et al. |
| 2014/0368793 A1 | 12/2014 | Friedman et al. |
| 2015/0062558 A1 | 3/2015 | Koppal et al. |
| 2015/0102981 A1 | 4/2015 | Lee et al. |
| 2015/0181096 A1 | 6/2015 | Kasai et al. |
| 2015/0212326 A1 | 7/2015 | Kress et al. |
| 2015/0288944 A1 | 10/2015 | Nistico et al. |
| 2016/0005179 A1 | 1/2016 | Petyushko et al. |
| 2016/0371886 A1 | 12/2016 | Thompson et al. |
| 2017/0160798 A1 | 6/2017 | Lanman et al. |

FOREIGN PATENT DOCUMENTS

| | | |
|---|---|---|
| KR | 10-2013-0011692 A | 1/2013 |
| KR | 10-2014-0144510 A | 12/2014 |

OTHER PUBLICATIONS

PCT International Search Report and Written Opinion, PCT Application No. PCT/US2016/059938, Dec. 20, 2016, 12 pages.

PCT International Search Report and Written Opinion, PCT Application No. PCT/US2016/017397, Aug. 16, 2016, 21 pages.

U.S. Appl. No. 15/407,701, filed Jan. 17, 2017, Inventors Nicholas Daniel Trail et al.

U.S. Appl. No. 15/366,412, filed Dec. 1, 2016, Inventor Nicholas Daniel Trail.

Machine translation of JP 2014-219521, published Nov. 20, 2014, 15 pages.

United States Office Action, U.S. Appl. No. 15/335,634, Dec. 14, 2017, 14 pages.

EYE TRACKING USING STRUCTURED LIGHT

RELATED APPLICATIONS

This application is a continuation of U.S. patent application Ser. No. 15/335,634 filed Oct. 27, 2016, which claims the benefit of U.S. Provisional Patent Application No. 62/249,852 filed on Nov. 2, 2015, the content of which are incorporated by reference in its entirety herein.

BACKGROUND

The present disclosure generally relates to eye tracking, and specifically relates to using structured light for eye tracking in virtual reality and/or augmented reality applications.

Eye tracking refers to the process of detecting the direction of a user's gaze, which may comprise detecting the angular orientation of the eye in 3-dimensional (3D) space. Eye tracking may further comprise detecting the location of the eye (e.g., the center of the eye), the torsion (i.e., the roll of the eye about the pupillary axis) of the eye, the shape of the eye, the current focal distance of the eye, the dilation of the pupil, other features of the eye's state, or some combination thereof. One known technique for eye tracking is capturing video images of a user and identifying the orientation of the user's pupils using a machine vision algorithm. However, this technique requires substantial computing resources, and is susceptible to occlusion of the eye by eyelashes and eyelids. Furthermore, this method is dependent on the contrast between the iris and the pupil, which is not invariant across users. Thus, video based pupil tracking may not be able to accurately track the eyes of certain users. In the context of a head-mounted display (HMD), such as in a virtual reality headset, this technique has additional drawbacks. The type of camera used to capture the images needed for this method of tracking may be relatively expensive or large. Similarly, this technique may place constraints on the proximity of the camera to the user's eye. Furthermore, this technique may perform poorly when the camera is located off the axis of the user's gaze. However, when eye tracking is used in an HMD, it may be preferred that the detection element of the eye tracking system be small, be close to the eye, and be off the axis of the user's gaze.

SUMMARY

An eye tracking unit for tracking the orientation and/or position of a user's eye is described. The eye tracking unit includes one or more structured light emitters and one or more cameras. In some embodiments, the eye tracking system or elements thereof may be part of a head-mounted display, e.g., as part of a virtual reality system. The one or more structured light emitters illuminate the eye with a structured light pattern (e.g., a pattern of infrared radiation). The one or more cameras capture images (e.g., capture images as video stream) of the eye illuminated with the structured light pattern. Parallax between the emitter and the camera may result in distortion in an image (e.g., a frame of a video stream) of the illumination pattern. In some embodiments, the eye tracking unit detects the shape of a portion of the surface of the eye upon which the structured light is incident based on the distortion apparent in the captured image. Based on a comparison of the detected shape of the eye to the model, the eye tracking unit estimates the orientation of the eye. Estimating the orientation of the eye may include, for example, determining the yaw, pitch, and roll rotation for the eye and a translation vector for the eye. In some embodiments, estimating the orientation of the eye comprises estimating the direction of the foveal axis of the eye. By estimating a direction of a pupillary axis of the eye and using an offset between the pupillary and foveal axes, the direction of the foveal axis may be estimated indirectly. The estimated orientation may be used to, e.g., determine gaze direction, inter-pupillary distance, etc.

In some embodiments, before eye tracking begins, the system may be calibrated by training a model of the user's eye. Training the model may include controlling an electronic display to display a visual indicator at a position on the electronic display; capturing, by the camera, a second image of a second distorted illumination pattern projected by the emitter onto the eye; and training the model based on the captured second image and based on the position of the visual indicator.

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

DETAILED DESCRIPTION

System Overview

Figure 1:
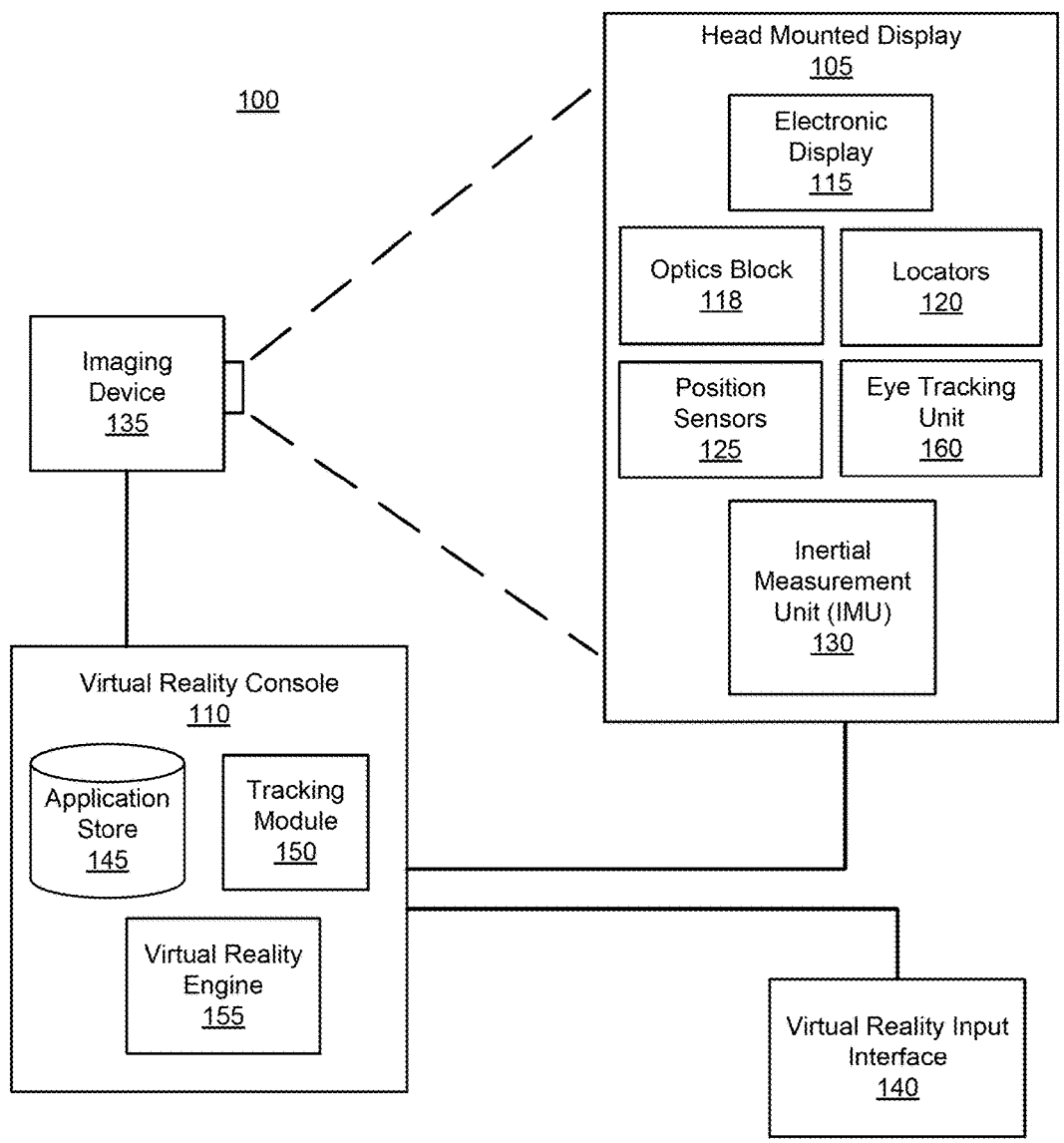
FIG. 1 is a diagram of a system environment including a virtual reality system, in accordance with an embodiment.

FIG. 1 is a block diagram of a virtual reality (VR) system environment 100 in which a VR console 110 operates. The system environment 100 shown by FIG. 1 comprises a HMD 105, an imaging device 135, and a VR input interface 140 that are each coupled to the VR console 110. While FIG. 1 shows an example system environment 100 including one HMD 105, one imaging device 135, and one VR input interface 140, in other embodiments any number of these components may be included in the system environment 100. For example, there may be multiple HMDs 105 each having an associated VR input interface 140 and being monitored by one or more imaging devices 135, with each HMD 105, VR input interface 140, and imaging devices 135 communicating with the VR console 110. In alternative configurations, different and/or additional components may be included in the system environment 100. Similarly, functionality of one or more of the components can be distributed among the components in a different manner than is described here. For example, some or all of the functionality of the VR console 110 may be contained within the HMD 105.

The HMD 105 is a head-mounted display that presents media to a user. Examples of media presented by the HMD 105 include one or more images, video, audio, or some combination thereof. In some embodiments, audio is presented via an external device (e.g., speakers and/or headphones) that receives audio information from the HMD 105, the VR console 110, or both, and presents audio data based on the audio information. Some embodiments of the HMD 105 are further described below in conjunction with FIGS. 2 and 3. The HMD 105 may comprise one or more rigid bodies, which may be rigidly or non-rigidly coupled to each other together. A rigid coupling between rigid bodies causes the coupled rigid bodies to act as a single rigid entity. In contrast, a non-rigid coupling between rigid bodies allows the rigid bodies to move relative to each other. In some embodiments, the HMD 105 may also act as an augmented reality (AR) HMD. In these embodiments, the HMD 105 augments views of a physical, real-world environment with computer-generated elements (e.g., images, video, sound, etc.).

The HMD 105 includes an electronic display 115, an optics block 118, one or more locators 120, one or more position sensors 125, an inertial measurement unit (IMU) 130, and an eye tracking unit 160. Some embodiments of the HMD 105 have different components than those described here. Similarly, the functions can be distributed among other components in the VR system environment 100 in a different manner than is described here. For example, some of the functions of the eye tracking unit 160 may be performed by the VR console 110. The electronic display 115 displays images to the user in accordance with data received from the VR console 110.

The optics block 118 magnifies received light from the electronic display 115, corrects optical errors associated with the image light, and the corrected image light is presented to a user of the HMD 105. The optical element is an optical element, such as an aperture, a Fresnel lens, a convex lens, a concave lens, a filter, or any other suitable optical element that affects the image light emitted from the electronic display 115. Moreover, the optics block 118 may include combinations of different optical elements. In some embodiments, one or more of the optical elements in the optics block 118 may have one or more coatings, such as partial reflectors or anti-reflective coatings.

Magnification of the image light by the optics block 118 allows the electronic display 115 to be physically smaller, weigh less, and consume less power than larger displays. Additionally, magnification may increase a field of view of the displayed media. For example, the field of view of the displayed media is such that the displayed media is presented using almost all (e.g., 110° diagonal), and in some cases all, of the user's instantaneous field of view. In some embodiments, the optics block 118 is designed so its effective focal length is larger than the spacing to the electronic display 115, which magnifies the image light projected by the electronic display 115. Additionally, in some embodiments, the amount of magnification may be adjusted by adding or removing optical elements.

The optics block 118 may be designed to correct one or more types of optical error. Examples of optical error include: two dimensional optical errors, three dimensional optical errors, or some combination thereof. Two dimensional errors are optical aberrations that occur in two dimensions. Example types of two dimensional errors include: barrel distortion, pincushion distortion, longitudinal comatic aberration, transverse chromatic aberration, or any other type of two-dimensional optical error. Three dimensional errors are optical errors that occur in three dimensions. Example types of three dimensional errors include spherical aberration, chromatic aberration, field curvature, astigmatism, or any other type of three-dimensional optical error. In some embodiments, content provided to the electronic display 115 for display is pre-distorted, and the optics block 118 corrects the distortion when it receives image light from the electronic display 115 generated based on the content.

The locators 120 are objects located in specific positions on the HMD 105 relative to one another and relative to a specific reference point on the HMD 105. A locator 120 may be a light emitting diode (LED), a corner cube reflector, a reflective marker, a type of light source that contrasts with an environment in which the HMD 105 operates, or some combination thereof. In embodiments where the locators 120 are active (i.e., an LED or other type of light emitting device), the locators 120 may emit light in the visible band (~380 nm to 750 nm), in the infrared (IR) band (~750 nm to 1700 nm), in the ultraviolet band (10 nm to 380 nm), some other portion of the electromagnetic spectrum, or some combination thereof.

In some embodiments, the locators 120 are located beneath an outer surface of the HMD 105, which is transparent to the wavelengths of light emitted or reflected by the locators 120 or is thin enough not to substantially attenuate the wavelengths of light emitted or reflected by the locators 120. Additionally, in some embodiments, the outer surface or other portions of the HMD 105 are opaque in the visible band of wavelengths of light. Thus, the locators 120 may emit light in the IR band under an outer surface that is transparent in the IR band but opaque in the visible band.

The IMU 130 is an electronic device that generates fast calibration data based on measurement signals received from one or more of the position sensors 125. A position sensor 125 generates one or more measurement signals in response to motion of the HMD 105. Examples of position sensors 125 include: one or more accelerometers, one or more gyroscopes, one or more magnetometers, another suitable type of sensor that detects motion, a type of sensor used for error correction of the IMU 130, or some combination thereof. The position sensors 125 may be located external to the IMU 130, internal to the IMU 130, or some combination thereof.

Based on the one or more measurement signals from one or more position sensors 125, the IMU 130 generates fast calibration data indicating an estimated position of the HMD 105 relative to an initial position of the HMD 105. For example, the position sensors 125 include multiple accelerometers to measure translational motion (forward/back, up/down, left/right) and multiple gyroscopes to measure rotational motion (e.g., pitch, yaw, roll). In some embodiments, the IMU 130 rapidly samples the measurement signals and calculates the estimated position of the HMD 105 from the sampled data. For example, the IMU 130 integrates the measurement signals received from the accelerometers over time to estimate a velocity vector and integrates the velocity vector over time to determine an estimated position of a reference point on the HMD 105. Alternatively, the IMU 130 provides the sampled measurement signals to the VR console 110, which determines the fast calibration data. The reference point is a point that may be used to describe the position of the HMD 105. While the reference point may generally be defined as a point in space;

however, in practice the reference point is defined as a point within the HMD 105 (e.g., a center of the IMU 130).

The IMU 130 receives one or more calibration parameters from the VR console 110. As further discussed below, the one or more calibration parameters are used to maintain tracking of the HMD 105. Based on a received calibration parameter, the IMU 130 may adjust one or more IMU parameters (e.g., sample rate). In some embodiments, certain calibration parameters cause the IMU 130 to update an initial position of the reference point so it corresponds to a next calibrated position of the reference point. Updating the initial position of the reference point as the next calibrated position of the reference point helps reduce accumulated error associated with the determined estimated position. The accumulated error, also referred to as drift error, causes the estimated position of the reference point to "drift" away from the actual position of the reference point over time.

The eye tracking unit 160 estimates the angular orientation of the user's eye. The orientation of the eye corresponds to the direction of the user's gaze within the HMD 105. The orientation of the user's eye is defined herein as the direction of the foveal axis, which is the axis between the fovea (an area on the retina of the eye with the highest concentration of photoreceptors) and the center of the eye's pupil. In general, when a user's eyes are fixed on a point, the foveal axes of the user's eyes intersect that point. The pupillary axis is another axis of the eye which is defined as the axis passing through the center of the pupil which is perpendicular to the corneal surface. The pupillary axis does not, in general, directly align with the foveal axis. Both axes intersect at the center of the pupil, but the orientation of the foveal axis is offset from the pupillary axis by approximately −1° to 8° laterally and ±4° vertically. Because the foveal axis is defined according to the fovea, which is located in the back of the eye, the foveal axis can be difficult or impossible to detect directly in some eye tracking embodiments. Accordingly, in some embodiments, the orientation of the pupillary axis is detected and the foveal axis is estimated based on the detected pupillary axis.

In general, movement of an eye corresponds not only to an angular rotation of the eye, but also to a translation of the eye, a change in the torsion of the eye, and/or a change in shape of the eye. The eye tracking unit 160 may also detect translation of the eye: i.e., a change in the position of the eye relative to the eye socket. In some embodiments, the translation of the eye is not detected directly, but is approximated based on a mapping from a detected angular orientation. Translation of the eye corresponding to a change in the eye's position relative to the detection components of the eye tracking unit may also be detected. Translation of this type may occur, for example, due to shift in the position of the HMD 105 on a user's head. The eye tracking unit 160 may also detect the torsion of the eye, i.e., rotation of the eye about the pupillary axis. The eye tracking unit 160 may use the detected torsion of the eye to estimate the orientation of the foveal axis from the pupillary axis. The eye tracking unit 160 may also track a change in the shape of the eye, which may be approximated as a skew or scaling linear transform or a twisting distortion (e.g., due to torsional deformation). The eye tracking unit 160 may estimate the foveal axis based on some combination of the angular orientation of the pupillary axis, the translation of the eye, the torsion of the eye, and the current shape of the eye.

The eye tracking unit 160 includes at least one emitter which projects a structured light pattern on all or a portion of the eye. This pattern then is then projected onto to the shape of the eye, which may produce a perceived distortion in the structured light pattern when viewed from an offset angle. The eye tracking unit 160 also includes at least one camera which detects the distortions (if any) of the light pattern projected onto the eye. A camera, oriented on a different axis than the emitter, captures the illumination pattern on the eye. This process is denoted herein as "scanning" the eye. By detecting the deformation of the illumination pattern on the surface of the eye, the eye tracking unit 160 can determine the shape of the portion of the eye scanned. The captured distorted light pattern is therefore indicative of the 3D shape of the illuminated portion of the eye. By deriving the 3D shape of the portion of the eye illuminated by the emitter, the orientation of the eye can be derived. The eye tracking unit can also estimate the pupillary axis, the translation of the eye, the torsion of the eye, and the current shape of the eye based on the image of the illumination pattern captured by the camera.

As the orientation may be determined for both eyes of the user, the eye tracking unit 160 is able to determine where the user is looking. The HMD 105 can use the orientation of the eye to, e.g., determine an inter-pupillary distance (IPD) of the user, determine gaze direction, introduce depth cues (e.g., blur image outside of the user's main line of sight), collect heuristics on the user interaction in the VR media (e.g., time spent on any particular subject, object, or frame as a function of exposed stimuli), some other function that is based in part on the orientation of at least one of the user's eyes, or some combination thereof. Determining a direction of a user's gaze may include determining a point of convergence based on the determined orientations of the user's left and right eyes. A point of convergence may be the point that the two foveal axes of the user's eyes intersect (or the nearest point between the two axes). The direction of the user's gaze may be the direction of a line through the point of convergence and though the point halfway between the pupils of the user's eyes. The eye tracking unit 160 is further described below in conjunction with FIG. 3 and FIG. 4.

The imaging device 135 generates slow calibration data in accordance with calibration parameters received from the VR console 110. Slow calibration data includes one or more images showing observed positions of the locators 120 that are detectable by the imaging device 135. The imaging device 135 may include one or more cameras, one or more video cameras, any other device capable of capturing images including one or more of the locators 120, or some combination thereof. Additionally, the imaging device 135 may include one or more hardware and software filters (e.g., used to increase signal to noise ratio). The imaging device 135 is configured to detect light emitted or reflected from locators 120 in a field of view of the imaging device 135. In embodiments where the locators 120 include passive elements (e.g., a retroreflector), the imaging device 135 may include a light source that illuminates some or all of the locators 120, which retro-reflect the light towards the light source in the imaging device 135. Slow calibration data is communicated from the imaging device 135 to the VR console 110, and the imaging device 135 receives one or more calibration parameters from the VR console 110 to adjust one or more imaging parameters (e.g., focal length, focus, frame rate, ISO, sensor temperature, shutter speed, aperture, etc.).

The VR input interface 140 is a device that allows a user to send action requests to the VR console 110. An action request is a request to perform a particular action. For example, an action request may be to start or end an application or to perform a particular action within the application. The VR input interface 140 may include one or more input devices. Example input devices include: a keyboard, a mouse, a game controller, or any other suitable device for receiving action requests and communicating the received action requests to the VR console 110. An action request received by the VR input interface 140 is communicated to the VR console 110, which performs an action corresponding to the action request. In some embodiments, the VR input interface 140 may provide haptic feedback to the user in accordance with instructions received from the VR console 110. For example, haptic feedback is provided when an action request is received, or the VR console 110 communicates instructions to the VR input interface 140 causing the VR input interface 140 to generate haptic feedback when the VR console 110 performs an action.

The VR console 110 provides media to the HMD 105 for presentation to the user in accordance with information received from one or more of: the imaging device 135, the HMD 105, and the VR input interface 140. In the example shown in FIG. 1, the VR console 110 includes an application store 145, a tracking module 150, and a virtual reality (VR) engine 155. Some embodiments of the VR console 110 have different modules than those described in conjunction with FIG. 1. Similarly, the functions further described below may be distributed among components of the VR console 110 in a different manner than is described here.

The application store 145 stores one or more applications for execution by the VR console 110. An application is a group of instructions, that when executed by a processor, generates content for presentation to the user. Content generated by an application may be in response to inputs received from the user via movement of the HMD 105 or the VR input interface 140. Examples of applications include: gaming applications, conferencing applications, video playback application, or other suitable applications.

The tracking module 150 calibrates the sensors of the VR system environment 100 using one or more calibration parameters and may adjust one or more calibration parameters to reduce error in determination of the position of the HMD 105. For example, the tracking module 150 adjusts the focus of the imaging device 135 to obtain a more accurate position for observed locators on the HMD 105. Moreover, calibration performed by the tracking module 150 also accounts for information received from the IMU 130. Additionally, if tracking of the HMD 105 is lost (e.g., the imaging device 135 loses line of sight of at least a threshold number of the locators 120), the tracking module 150 re-calibrates some or all of the system environment 100.

The tracking module 150 tracks movements of the HMD 105 using slow calibration information from the imaging device 135. The tracking module 150 determines positions of a reference point of the HMD 105 using observed locators from the slow calibration information and a model of the HMD 105. The tracking module 150 also determines positions of a reference point of the HMD 105 using position information from the fast calibration information. Additionally, in some embodiments, the tracking module 150 may use portions of the fast calibration information, the slow calibration information, or some combination thereof, to predict a future location of the HMD 105. The tracking module 150 provides the estimated or predicted future position of the HMD 105 to the VR engine 155.

The VR engine 155 executes applications within the system environment 100 and receives position information, acceleration information, velocity information, predicted future positions, or some combination thereof of the HMD 105 from the tracking module 150. Based on the received information, the VR engine 155 determines content to provide to the HMD 105 for presentation to the user. For example, if the received information indicates that the user has looked to the left, the VR engine 155 generates content for the HMD 105 that mirrors the user's movement in a virtual environment. Additionally, the VR engine 155 performs an action within an application executing on the VR console 110 in response to an action request received from the VR input interface 140 and provides feedback to the user that the action was performed. The provided feedback may be visual or audible feedback via the HMD 105 or haptic feedback via the VR input interface 140.

Figure 2:
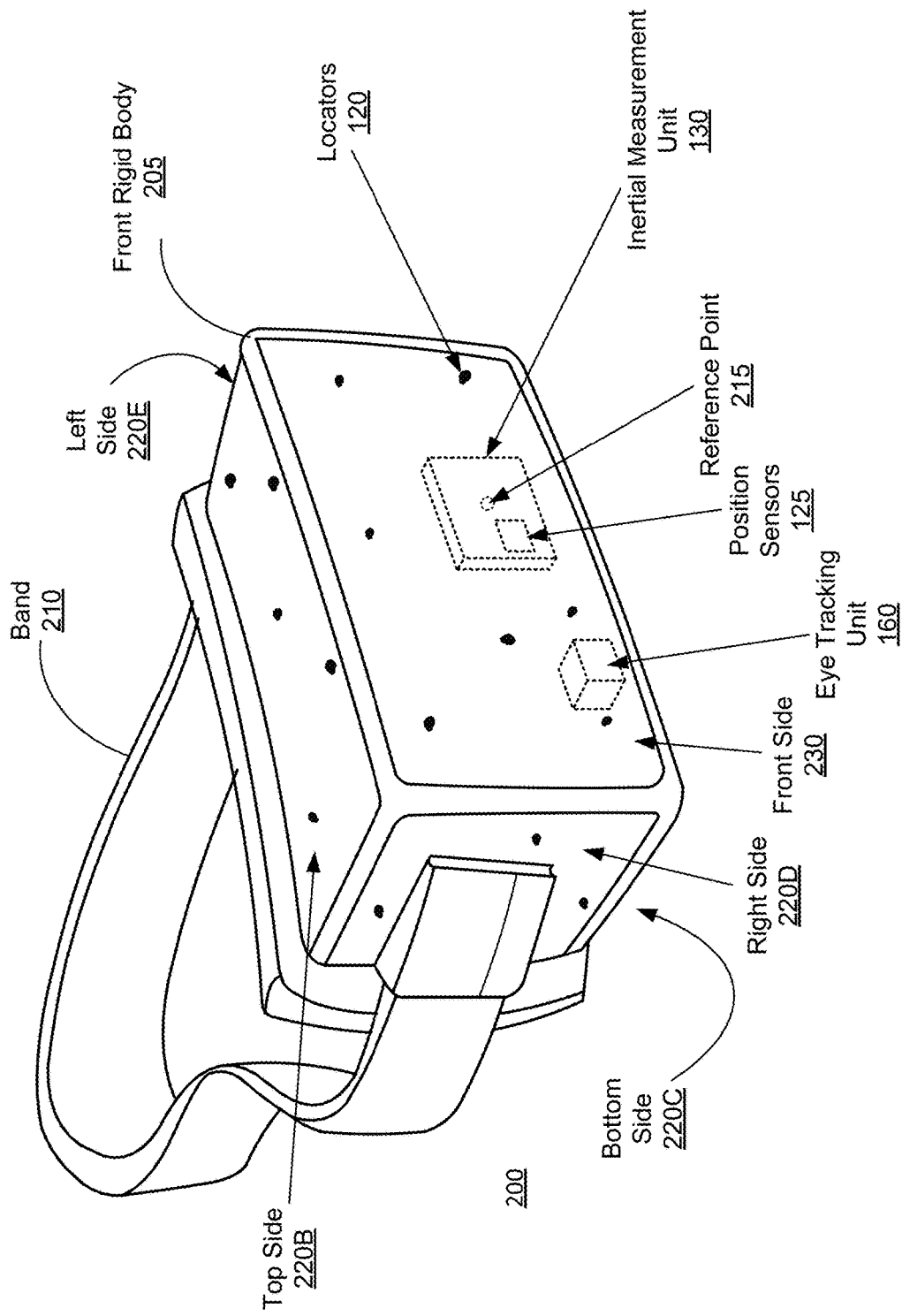
FIG. 2 is a diagram of a HMD, in accordance with an embodiment.

FIG. 2 is a diagram of an HMD, in accordance with an embodiment. The HMD 200 is an embodiment of the HMD 105, and includes a front rigid body 205 and a band 210. The front rigid body 205 includes an electronic display element of the electronic display 115 (not shown in FIG. 2), the optics block 118 (not shown in FIG. 2), the IMU 130, the one or more position sensors 125, an eye tracking unit 160, and the locators 120. In the embodiment shown by FIG. 2, the position sensors 125 are located within the IMU 130, and neither the IMU 130 nor the position sensors 125 are visible to the user.

The locators 120 are located in fixed positions on the front rigid body 205 relative to one another and relative to a reference point 215. In the example of FIG. 2, the reference point 215 is located at the center of the IMU 130. Each of the locators 120 emit light that is detectable by the imaging device 135. The locators 120, or portions of the locators 120, are located on a front side 220A, a top side 220B, a bottom side 220C, a right side 220D, and a left side 220E of the front rigid body 205 in the example of FIG. 2.

The HMD 200 includes an eye tracking unit 160. The eye tracking unit 160 may include a structured light emitter to project a structured light pattern onto the user's eye and a camera to detect the illuminated portion of the eye. The emitter and the camera may be located off the axis of the user's gaze. In FIG. 2, the eye tracking unit 160 is located below the axis of the user's gaze, although the eye tracking unit 160 can alternately be placed elsewhere. Also, in some embodiments, there is at least one eye tracking unit for the left eye of the user and at least one tracking unit for the right eye of the user.

Figure 3:
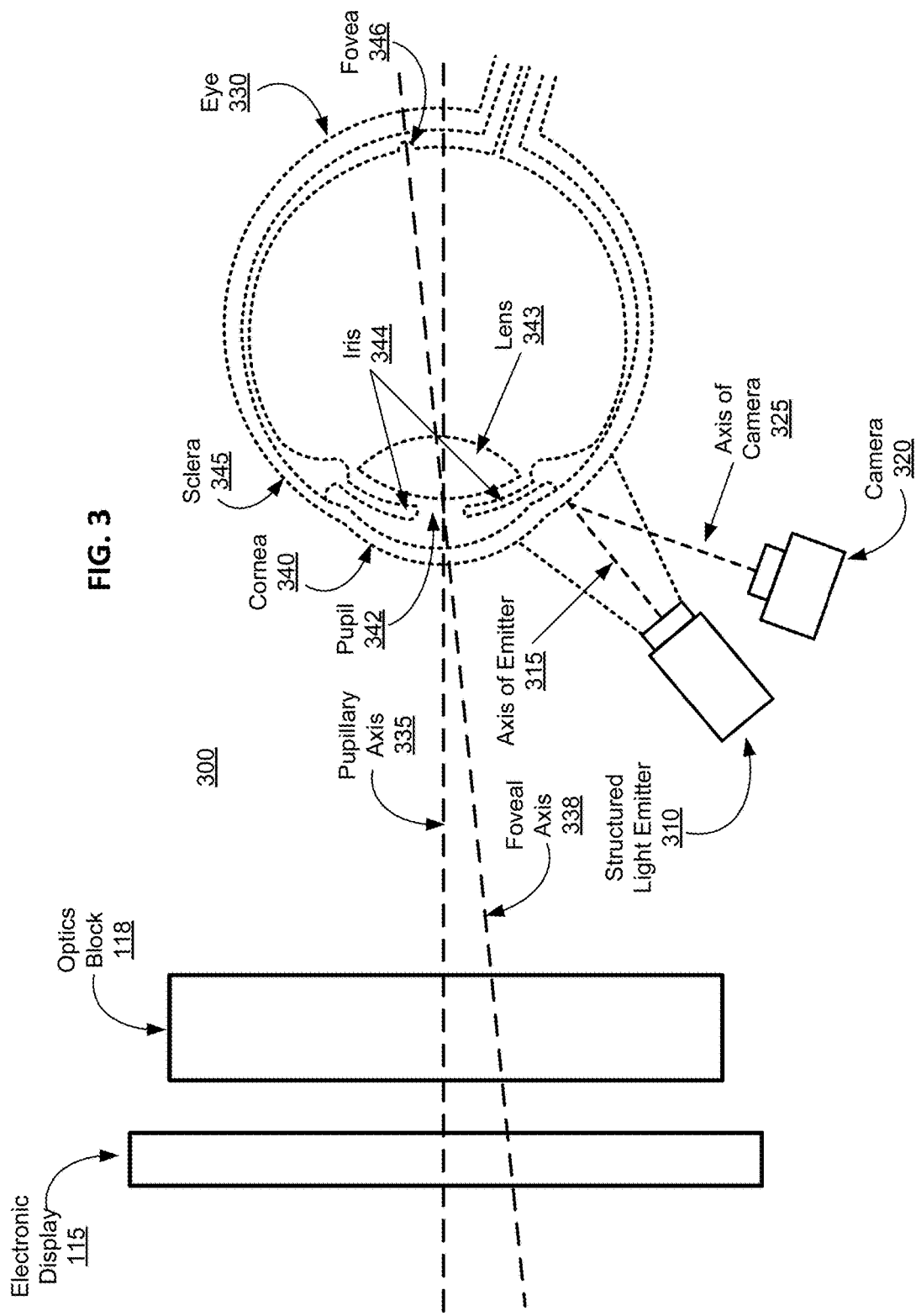
FIG. 3 is a diagram of a structured light system including a structured light emitter and camera, in accordance with an embodiment.

FIG. 3 depicts a structured light eye tracking system 300 which tracks the position of the user's eye 330 by repeatedly scanning the eye 330. FIG. 3 includes a cross-section of the eye 330. In some embodiments, the structured light eye tracking system 300 is a component of the eye tracking unit 160 of an HMD (e.g., HMD 105 or HMD 200). In alternate embodiments, the structured light eye tracking system 300 is part of an AR HMD, a VR/AR system that is not a HMD, or some other system which employs eye tracking. The structured light eye tracking system 300 includes a structured light emitter 310 and a camera 320. FIG. 3 depicts a single structured light emitter 310 and a single camera 320 detecting the orientation of a single eye 330. However, in alternate embodiments, multiple structured light emitters or multiple cameras may be employed for a single eye. Similarly, for each of the user's eyes, a corresponding structured light emitter and camera may be employed.

The structured light emitter 310 emits a structured light pattern, P, onto a portion of a user's eye. The structured light emitter 310 includes an infrared (IR) light source and a structured light element. The IR light source (e.g., laser diode, light emitting diode, etc.) emits IR light (e.g., 850 nm) toward the structured light element, which transforms the IR light into structured IR light (in angular coordinates). In some embodiments, the IR light source of the structured light emitter 310 emits a continuous spectrum of IR light, to reduce the coherence of the source. In some embodiments, the structured light emitter 310 outputs a single frequency or a narrowband spectrum of light. In alternate embodiments, the structured light emitter 310 outputs N single frequencies or N narrow bands with distinct center-frequencies.

The structured light element is an optical element that when illuminated by the IR light source outputs structured light. The structured light element may be, e.g., an apodization and/or phase mask, a diffractive element, birefringent plate, some other optical element that when illuminated by the IR light source outputs structured light, or some combination thereof. Additionally, in some embodiments, the IR light source may be modulated in time, frequency, or both. Although the structured light emitter 310 is described herein as emitting structured light in the IR spectrum, alternate embodiments include a structured light emitter 310 which emits light in non-IR wavelengths, such as the visible spectrum (~390 nm to 700 nm).

In the context of a single eye of a user, the structured light pattern, P, is incident upon the surface of a portion of the eye 330. The structured light pattern distorts based in part on, e.g., the geometry of the illuminated surface and emitter to camera geometry, to form a distorted illumination pattern. The variation in the distorted illumination pattern is indicative of the 3D structure of a portion of the surface of the eye 330. In some embodiments, the portion of the eye covers the sclera 345, the cornea 340, or both. In some embodiments, multiple structured light emitters project structured light patterns onto a single eye 330. In some embodiments, a first structured light emitter projects a first structured light pattern onto one of the user's eyes and a second structured light emitter projects a second structured light pattern onto the other eye.

The camera 320 detects the distorted light pattern on the portion of the eye 330 illuminated by the structured light emitter 310. The camera 320 may be an infrared camera (i.e., a camera designed to capture images in the infrared frequency). The camera may be a near-infrared camera with digital image sensors sensitive to the bandwidth of light emitted by the structured light emitter 310. The camera 320 includes a CCD or CMOS digital image sensor and an optical element. The optical element may be one or more lenses, a high-pass, low-pass, or band-pass filter, a polarizer, an aperture stop, a diaphragm, some other optical element suitable for processing IR light, or some combination thereof. The optical element outputs light which is captured and converted into a digital signal by the CCD or CMOS digital sensor.

The camera 320 detects the distorted illumination pattern and converts the captured light into a digital image, I. The digital image, I, may be a binary image (i.e., an image in which each pixel has a binary value) or a single channel image (an image in which each pixel maps to a single floating-point or integer value). In embodiments in which the structured light emitter 310 emits patterns of light of N distinct frequencies or N distinct center-frequencies, I may be an N-channel image.

The camera 320 may be specially configured to detect electromagnetic radiation within the band that the structured light emitter 310 projects. The camera 320 may employ a narrowband band-pass filter which filters out light outside of the spectrum emitted by the structured light emitter 310. When this band is relatively small, the signal-to-noise ratio (SNR) is large, which allows images to be captured by the camera 320 rapidly. In some embodiments, the camera 320 is a high-frequency camera, but when high frequency is not needed, the camera 320 may capture images at a frequency less than the maximum frequency. The frame rate with which images are captured by the camera 320 is generally 60 Hz of greater, although some embodiments may capture images at a slower rate. The structured light emitter 310 may be configured to only emit light when the camera 320 is capturing images.

The camera 320 may capture images at a first frequency during normal operating conditions, but certain conditions may trigger the camera 320 to capture images at a higher frequency. For example, when the eye tracking unit 160 cannot detect the orientation of the eye 330, the scan may be considered a "bad scan." A "bad scan" may be triggered by the user blinking. In the case of a "bad scan," the scan may be disregarded and the camera 320 can be triggered to immediately capture another scan of the eye 330 until a successful scan is recorded. In this manner, the eye tracking unit 160 can ensure that the tracking of the eye's orientation is as accurate and current as possible, without requiring unnecessary computation and power consumption.

The eye 330 includes a cornea 340, a pupil 342, a lens 343, an iris 344, a sclera 345, and a fovea 346. The sclera 345 is the relatively opaque (usually visibly white) outer portion of the eye 330, which is often referred to as the "white of the eye." The cornea 340 is the curved surface covering the iris and the pupil of the eye. The cornea 340 is essentially transparent in the visible band (~380 nm to 750 nm) of the electromagnetic spectrum, and the near-infrared region (up to approximately 1,400 nanometers). The lens 343 is a transparent structure which serves to focus light at the retina (the back of the eye 330). The iris 344 is a thin, colored, circular diaphragm concentric with the pupil 342. The iris 344 is the colored portion of the eye which contracts to alter the size of the pupil 342, a circular hole through which light enters the eye 330. The fovea 346 is an indent on the retina. The fovea 346 corresponds to the area of highest visual acuity.

Due to the rotation and movement of the eye 330, the portion of the eye's surface illuminated by the structured light emitter 310 may be variable. In some embodiments, the structured light emitter 310 projects light in a spectrum where the cornea 340 is nearly transparent (e.g., the near IR or visible spectrum). In the case in which part of the structured light pattern passes through the cornea 340 and illuminates the iris 344, the resultant illumination pattern on the approximately planar interface of the iris is distorted according to some optical power of the surface of the cornea 340. For the region within the pupil 342 of the iris 344, the intensity of the illumination pattern is significantly reduced. In some embodiments, the illumination pattern upon the pupil 342 is considered to be negligible. The eye tracking unit 160 may identify a distorted circular unilluminated portion in the image captured by the camera 320 as the pupil 342 and determine the angular orientation of the eye 330 based on the position of the pupil 342.

In some embodiments, the structured light emitter 310 projects light in a spectrum where the cornea 340 is nearly opaque (e.g., IR light with a wavelength greater than 1.5 μm) and the camera 320 (e.g., a long IR camera) detects the resultant illumination pattern. When the cornea 340 is illuminated by the structured light pattern, the eye tracking unit 160 may estimate the eye's angular orientation and/or translation based on the curvature of the cornea 340. Because the cornea 340 projects outward from the approximately ellipsoidal sclera 345, the eye tracking unit 160 may estimate an orientation of the eye 330 by detecting the curvature of the cornea 340. The eye tracking unit 160 may also estimate the eye's orientation by detecting the cornea-sclera interface, i.e., the roughly circular outline where the surface of the cornea 340 and the surface of the sclera 345 intersect. The eye tracking unit 160 may also estimate the eye's orientation by detecting the vertex of the cornea 340, i.e., the part of the cornea 340 that extends furthest from the center of the eye 330.

The eye's pupillary axis 335 and foveal axis 338 are depicted in FIG. 3. The pupillary axis 335 and foveal axis 338 change as the eye 330 moves. In FIG. 3, the eye 330 is depicted with a horizontal pupillary axis 335. Accordingly, the foveal axis 338 in FIG. 3 points about 6° below the horizontal plane. FIG. 3 also depicts the axis of the emitter 315 and the axis of the camera 325. FIG. 3 depicts an embodiment in which the structured light emitter 310 and the camera 320 are not on either the pupillary axis 335 or the foveal axis 338. The structured light emitter 310 and the camera 320 may be outside the visual field of the eye 330.

Figure 4:
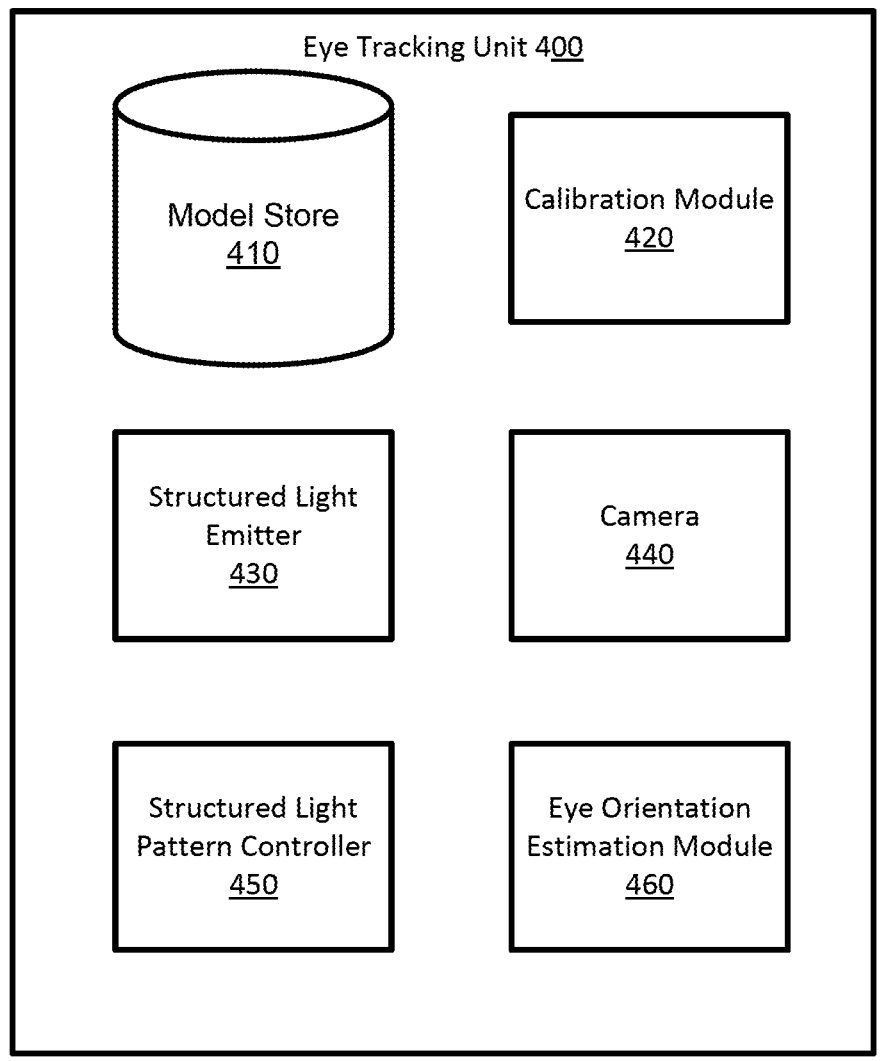
FIG. 4 is a block diagram of an eye tracking unit, in accordance with an embodiment.

FIG. 4 is a high-level block diagram illustrating a detail view of an eye tracking unit 400 according to one embodiment. Some embodiments of the eye tracking unit 400 have different components than those described here. Similarly, the functions can be distributed among the components in a different manner than is described here. The eye tracking unit 400 includes a model store 410, a calibration module 420, a structured light emitter 430, a camera 440, a structured light pattern controller 450, and an eye orientation estimation module 460. In some embodiments, the eye tracking unit 400 is the eye tracking unit 160 of the HMD 105. In other embodiments, the eye tracking unit 400 is part of some other system, such as an AR system, that tracks user eye movement. The eye tracking unit 400 may track both eyes of a user and may include multiple structured light emitters and multiple cameras. However, as in FIG. 3, the eye tracking unit 400 is described herein with respect to a single eye, a single structured light emitter 430, and a single camera 440.

The model store 410 is a memory that stores a model, M, of a user's eye, which is used to compare to the image I to estimate the current orientation of the eye. The model store 410 is a memory, such as a ROM, DRAM, SRAM, or some combination thereof. The model store 410 may be part of a larger digital memory of the virtual reality (VR) system environment 100. The model, M, stored in the model store 410 can be a 3D model of the eye's surface. In embodiments in which both of a user's eyes are scanned, the model store 410 may contain two model's $M_1$ and $M_2$: one for each eye.

In some embodiments, M is a 3D model which approximates the surface geometry of the eye. The 3D model may have two orthogonal axes defined about which the model of the eye rotates. Thus, the 3D model may incorporate two angles, $\alpha$ (yaw) and $\beta$ (pitch), which specify the orientation of the eye relative to the centered orientation of the eye (i.e., $\alpha=\beta=0°$ corresponds to the eye looking straight ahead). $\alpha$ and $\beta$ may correspond to the angular direction of the foveal axis. M may also incorporate a roll angle, $\gamma$, which corresponds to the roll of the eye (i.e., the torsion). M may further incorporate a translation vector $[x_0, y_0, z_0]^T$, which specifies a translation of the 3D model in a Cartesian coordinate system. In some embodiments, the angle of the pupillary axis or $(\alpha, \beta)$ is mapped to a translation vector, $[x_0, y_0, z_0]^T$. In embodiments in which detecting the orientation of the eye comprises detecting the pupil, M may incorporate a pupil diameter, d. In some embodiments, the foveal axis is calculated based on the angle of the pupillary axis, $[x_0, y_0, z_0]^T$, $\gamma$, and a parameter corresponding to the location of the fovea stored in M. In some embodiments, tracking the eye may constitute finding the values of $\alpha$ and $\beta$ which make the 3D model of the eye most closely fit the scanned portion of the eye. In some embodiments, tracking the eye comprises matching the scanned portion of the eye to M using some combination of $\alpha$ and $\beta$, the angle of the pupillary axis, $[x_0, y_0, z_0]^T$, $\gamma$, and d.

The model, M, may be a mathematical model of the 2D surface of the eye embedded in 3D space. M may be continuous, or may consist of discrete points. For example, in Cartesian space, the x, y, and z axes may correspond to the center axis of the eye, the horizontal axis orthogonal to the center axis of the eye, and the vertical axis, respectively. The model may include of a function, $X(y, z, \alpha, \beta)$, wherein every set of $(\alpha, \beta)$ generates a surface protruding into the x axis from the y-z plane. In some embodiments, $\alpha$ and $\beta$ correspond to the angles of a rotational transform applied to the surface in $\mathbb{R}^3$. For example, if $(x,y,z)=(0,0,0)$ corresponds to the point of rotation of the model of the eye, then this rotation may be represented by the rotation matrix $R_z(\alpha)R_y(\beta)$, where $R_z(\alpha)$ and $R_y(\beta)$ are yaw and pitch matrices, as conventionally defined. The model, M, may also include parameters corresponding to a translation of the eye and a torsion of the eye.

Similarly, M may include a function of polar coordinates, with a function of the form $R(\theta, \phi)$. If the origin of the polar coordinate system is defined as the point about which the eye rotates, then the model of the surface of the eye may be given by $R(\theta-\alpha, \phi-\beta)$.

In some embodiments, M is an image generating function rather than a mathematical model of a 3D surface. The model of the eye, M, can be an image generating function, $I_M(\alpha, \beta)$, which returns a 2D image for each value of $\alpha$ and $\beta$. $I_M(\alpha, \beta)$ may also include additional inputs such as translation vector and a roll angle ($\gamma$), such that some combination of $\alpha$, $\beta$, $\gamma$, and $[x_0, y_0, z_0]^T$ is mapped to an image. The image generating function, $I_M(\alpha, \beta)$, may select an image from a finite set of images stored in the model store 410. Alternately, $I_M(\alpha, \beta)$ may be a continuous function (i.e., approximately continuous, since it is being implemented via an integer, floating point, or alternate computer-implemented numeral scheme).

In some embodiments, M consists of a set of images, where each image is mapped to a value of $\alpha$ and $\beta$. In alternate embodiments, if the image generating function $I_M(\alpha, \beta)$ does not have an image for the exact values of $\alpha$ and $\beta$, then images that correspond to orientations close to $\alpha$ and $\beta$ can be interpolated together to create a composite image, which is returned by $I_M(\alpha, \beta)$. If multiple structured light patterns are used by the eye tracking unit 400, then model M should have an image generating function for each structured light pattern.

M may comprise a 3D model of the eye, which, along with an input structured light pattern, P, is used to generate an image. This image generating function, $I_M(\alpha, \beta, P)$, may be implemented by rendering a mathematical model of the structured light pattern (e.g., a ray model) on the 3D model of the eye. The image output by $I_M(\alpha, \beta, P)$ may be an approximation of the image expected to be captured by the camera 320 for the given values of $\alpha$, $\beta$, and P.

In some embodiments, rather than a generic surface, the model, M, consists of a number of parameters which approximately specify the shape of the eye. For example, these parameters could correspond to an average radius of the eye, an average radius of the sclera of the eye, a set of three parameters to approximate the shape of the sclera as a ellipsoid, a radius of the cornea of the eye, a measurement of the protrusion of the cornea from the sclera, a set of parameters specifying the shape of the cornea, and a point of rotation for the eye. Additional parameters may be used to account for deviations from the ideal model specified by the parameters. For example, a bulge on the eye's surface caused by a blood vessel may be accounted for in M via these additional parameters.

The calibration module 420 generates or trains the model M prior to eye tracking during a calibration sequence. The calibration module 420 is a software module implemented on one or more processors, a dedicated hardware unit, or some combination thereof. The calibration sequence implemented by the calibration module 420 may involve using the camera 440 and the structured light emitter 430 to repeatedly scan the eye. In one embodiment, the user is instructed to look at a certain virtual object or visual indicator that is displayed on the electronic display 115 of the HMD 105. A portion of the eye can be scanned while the user is looking at the visual indicator. In this way, the eye tracking unit 400 can capture sample scans of the eye at known orientations of the eye. These sample scans can be interpolated into a model, M which is stored in the model store 410. Once the calibration module 420 has produced M, eye tracking may begin. In general, eye tracking with a model, M, trained for a specific user's eye is more accurate than eye tracking without such a model. In some embodiments, the calibration module 420 continues to update M during tracking. In some embodiments, the system may begin tracking with a nominal model M based on statistical norms of human eyes and 420 updates M during tracking.

The multiple scans of the eye 330 collected during the calibration sequence may be composited into a 3D model, a 3D model generating function, or an image generating function $I_M(\alpha, \beta)$. The 3D model or 3D model generating function may be calculated by converting the set of images captured by the camera 320 during calibration into a set of 3D surfaces, $\{S_1, \ldots, S_N\}$, which corresponds to a set of yaw values $\{\alpha_1, \ldots, \alpha_N\}$, and pitch values $\{\beta_1, \ldots \beta_N\}$, where $\{\alpha_1, \ldots, \alpha_N\}$ and $\{\beta_1, \ldots \beta_N\}$ correspond to the position of the visual object displayed on the display. $\{S_1, \ldots, S_N\}$, $\{\alpha_1, \ldots, \alpha_N\}$, and $\{\beta_1, \ldots \beta_N\}$ may be interpolated into a single 3D surface model generating function. In some embodiments, a set of error parameters $\{E_1, \ldots, E_N\}$ is also used to generate M. Each $E_i$ may be a function indicative of the reliability of each point on the surface at $S_i$. Alternately, $E_i$ may be a single value indicative of the reliability of $S_i$ as a whole. $E_i$ can be used to weigh $S_i$ so that the degree to which $S_i$ effects the model is based on $E_i$.

During calibration, in addition to creating the model of the eye, M, the calibration module 420 may also determine a pattern of light that is best suited for detecting the orientation of the eye among several candidate patterns. In some embodiments, a best structured light pattern may be determined for a given range of orientations of the eye. During eye tracking, the optimal structured light pattern may be projected onto the eye responsive to the previously detected orientation of the eye.

The structured light emitter 430 emits a pattern, P, of structured light, which is incident upon a portion of the eye. The geometry of the surface of the eye distorts the structured light pattern to form a distorted illumination pattern. The structured light emitter 430 may be the same structured light emitter 430 as the structured light emitter 310 depicted in FIG. 3.

The camera 440 detects the distorted illumination pattern. The camera 440 converts the captured light into a digital image, I. In some embodiments, the camera 440 is the camera 320. In embodiments in which the model of the eye, M, is an image generating function, $I_M(\alpha, \beta)$, the images generated by $I_M(\alpha, \beta)$ may be the same type of images as I (e.g., binary images, single-channel images, or multi-channel images). The images output by $I_M(\alpha, \beta)$ may also be of the same size (e.g., in pixels) as the image, I, output by the camera 440.

In some embodiments, a structured light pattern controller 450 controls the structured light emitter 430. The structured light pattern controller 450 is a software module implemented on one or more processors, a dedicated hardware unit, or some combination thereof. The structured light pattern controller 450 determines the structured light pattern, P, emitted. In some embodiments, the structured light emitter 430 always projects the same pattern, and the structured light pattern controller 450 simply controls whether or not the structured light emitter 430 emits light. In some embodiments, the structured light pattern controller 450 changes the structured light pattern to a different pattern in response to a report of a "bad scan." In some embodiments, the structured light pattern controller 450 selects the structured light pattern based on the previously reported orientation of the eye as reported by the eye tracking unit 400.

The eye orientation estimation module 460 receives the image, I, as an input and generates an estimate of the orientation of the eye based on a model, M, from the model store 410. The eye orientation estimation module 460 is a software module implemented on one or more processors, a dedicated hardware unit, or some combination thereof.

In some embodiments, the eye orientation estimation module 460 generates a 3D approximation of the surface of the eye, S, corresponding to the area of the eye illuminated by the structured light emitter 430. The eye orientation estimation module 460 uses the known structure of the projected structured light pattern, which can be received from the structured light pattern controller 450, to determine the distortion of the light caused by the shape of the eye's surface and the camera geometry. From the distortion, the eye orientation estimation module 460 attributes depth information to different portions of the image. Using the depth information the eye orientation estimation module 460 generates the approximation of the 3D surface of the eye, S. S may comprise, for example, a finite set of 3-dimensional points in Cartesian space, a finite set of points in polar coordinates, or a mathematical function defining a surface in $\mathbb{R}^3$. The eye orientation estimation module 460 may also output an error function, E, which gives an estimate indicative of the accuracy of a given point on the surface S. E may, for example, be a function which takes in 2-dimensional coordinates and returns an estimate of the standard deviation of that point's extension from a plane (in Cartesian coordinate system) or radius (in a polar coordinate system).

As an illustrative example of calculating S, consider a structured light pattern comprising an array of dots with pseudo-random positions. Supposing that the structured light pattern consists of N dots, wherein each dot has a negligibly small area, the light which generates each dot can be represented by a ray. If $r_i$ represents the ith ray (for $i \in \{1, \ldots, N\}$), then $r_i$ can be expressed as:

$$r_i = a_i \gamma_i + b_i = \begin{bmatrix} a_{i1} \\ a_{i2} \\ a_{i3} \end{bmatrix} \alpha_i + \begin{bmatrix} b_{i1} \\ b_{i2} \\ b_{i3} \end{bmatrix}$$

where $a_i, b_i \in \mathbb{R}^3$ and $\gamma_i$ is the dependent variable of the parametric equation. Each ray is incident upon the surface of the eye and intersects with the surface at a point $p_i \in \mathbb{R}^3$. This point is illuminated by the ray of light and this illumination is detected by one of K cameras. The kth of the K cameras detects this by capturing a ray of light originating from point $p_i$. This ray of light can be represented as $y_{ik}$ such that:

$$y_{ik} = c_{ik}\delta_i + d_{ik} = \begin{bmatrix} c_{ik1} \\ c_{ik2} \\ c_{ik3} \end{bmatrix}\beta_{ik} + \begin{bmatrix} d_{ik1} \\ d_{ik2} \\ d_{ik3} \end{bmatrix}$$

where $c_i, d_i \in \mathbb{R}^3$ and $\delta_{ik}$ is the dependent variable of the parametric equation. $r_i$ is known a priori and $y_{ik}$ can be found by a mapping algorithm which maps received pixel position on the kth camera to vectors $c_i, d_i$. Thus, because $p_i$ is the point at which $r_i = y_{ik}$ for all $k \in \{1, \ldots, K\}$. The following system can be solved to find $p_i$:

$$\begin{bmatrix} a_{i1} & c_{ik1} \\ a_{i2} & c_{ik2} \\ a_{i3} & c_{ik3} \end{bmatrix}\begin{bmatrix} \gamma_i & -\delta_{ik} \end{bmatrix} = \begin{bmatrix} d_{ik1} - b_{i1} \\ d_{ik2} - b_{i2} \\ d_{ik3} - b_{i3} \end{bmatrix}$$

However, the above system is an overdetermined system. Consequently, non-idealities in the measurements and a priori assumptions are likely to result in no exact solution existing. Nevertheless, an approximation can be found. One such approximation for $p_i$ is a an average of least square error approximations, $\hat{p}_i$. $\hat{p}_i$ can be calculated as follows:

$$\hat{x}_{ik} = [\hat{\gamma}_{ik} - \hat{\delta}_{ik}]^T = (A_{ik}^T A_{ik})^{-1} A_{ik}^T v_{ik}$$

Where $$A_{ik} = [a_i \ c_{ik}] = \begin{bmatrix} a_{i1} & c_{ik1} \\ a_{i2} & c_{ik2} \\ a_{i3} & c_{ik3} \end{bmatrix} \text{ and } v_{ik} = d_{ik} - b_i = \begin{bmatrix} d_{ik1} - b_{i1} \\ d_{ik2} - b_{i2} \\ d_{ik3} - b_{i3} \end{bmatrix}.$$

$$\hat{p}_i = \left(\frac{1}{K}\sum_{k=1}^{K}\hat{\gamma}_{ik}\right) a_i + b_i$$

By deriving, $\hat{p}_i$ for all $i \in \{1, \ldots N\}$, the system can calculate, with some granularity, the shape of the object upon which the pattern of structured light is incident. Thus S may be represented by the set of point $\{\hat{p}_1, \ldots, \hat{p}_N\}$ or may be derived from the set of points. This example is only intended to be an illustrative example of generating S. Different approximation techniques and different algorithmic approaches may be used. Also, different patterns of structured light, and algorithms suitable for those patterns of structured light, can be used. Algorithms suitable for 3D mapping with each pattern of structured light are known.

The surface approximation of the eye, S, can be used by the eye orientation estimation module 460 to compare to the model of the eye, M, retrieved from the model store 410. As noted above, the model, M, can be a 3D model of the eye's surface. The eye orientation estimation module 460 may perform a 2-dimensional correlation which correlates S (the 3D surface generated by scanning the eye) with M by varying the yaw, $\alpha$, and pitch, $\beta$, of the eye as dependent variables. For purposes of this description, $\alpha$ is defined as the horizontal angle of the eye, and $\beta$ is defined as the vertical angle of the eye, where $\alpha = \beta = 0°$ corresponds to the user looking straight ahead. The correct orientation of the eye may be determined to be the value of $\alpha$ and $\beta$ for which the model of the eye, M, most closely matches the surface approximation, S.

As an example, S may be a set of points in a polar coordinate system, $S = \{p_1, \ldots, p_N\}$, where $p_i = [\theta_i \ \phi_i \ r_i]^T$. The model, M, may take the form of a function of polar coordinates, $R_M(\theta, \phi)$, which returns a radius as a function of two angle $\theta$ and $\phi$, such that the origin of the coordinate system corresponds to origin of rotation of the eye. The orientation of the eye can be determined by iterating through a finite set of $\alpha$ and $\beta$ values in order to find the values of $(\alpha, \beta)$ which maximize the following:

$$\Sigma_{i=1}^{N}(r_i - \mu_r)(R_M(\theta_i - \alpha, \phi_i - \beta) - \mu_m)$$

where $\mu_r$ is the average radius of S $$\left(\text{i.e., } \mu_r = \frac{1}{N}\sum r_i\right)$$

and $\mu_m$ is the average radius of the surface defined by the function $R_M(\theta, \phi)$. There are many alternate methods which the eye orientation estimation module 460 may use to determine the values of $\alpha$ and $\beta$ for which M and S most closely match. Such methods are known to one skilled in the art.

In some embodiments, values from the set $\{(\alpha_1, \beta_1), \ldots, (\alpha_N, \beta_N)\}$ are used as inputs to determine the correlation between S and M. The values in this set may be restricted to a certain bounded region. The region may be defined by the range of movement of the eye. In some embodiments, the region is restricted to values within a certain angular distance from the previous calculated yaw and pitch. The region may be determined based on an upper bound value for the maximum speed of the eye. For example, because the maximum angular saccade speed of the human eye is about 900° per second, the region may be constrained to within 1000°/F of the previously detected orientation of the eye where F is the frame rate of the camera 440 in Hertz.

In some embodiments, an estimate of the surface of the eye, S, is not generated and the image, I, captured by the camera 440, is directly compared to the model, M by the eye orientation estimation module 460. M may be a mapping of images to values of yaw and pitch ($\alpha$ and $\beta$). In some embodiments, values of ($\alpha$, $\beta$) are mapped to model images by an image generating function which takes $\alpha$ and $\beta$ as inputs. Multiple model images, each corresponding to a different ($\alpha$, $\beta$) pair may be compared to the image, I, captured to the camera 440. The ($\alpha$, $\beta$) pair which corresponds to the model image that most closely matches I may be determined to be the orientation of the eye. In some embodiments, determining the ($\alpha$, $\beta$) pair which maps to the most closely matching model image may be done by a two dimensional correlator, where the correlation is performed with ($\alpha$, $\beta$) as the dependent variables.

The eye tracking unit 400 can be part of a VR system, such as that of the VR system environment 100 shown in FIG. 1. The eye tracking unit 400 can be part of a HMD 105, however, the modules of the eye tracking unit 400 responsible for controlling the structured light emitter 430 and processing the images received from the camera 440 need not be a part of the HMD 105. These components can be located on the virtual reality console 110. In some embodiments, processing data output by the eye tracking unit 400 is performed by one or more generic processors on the virtual reality console 110. In some embodiments, the eye tracking algorithms are implemented on specialized hardware. In some embodiments, some of the control and processing modules of the eye tracking unit 400 are part of the HMD 105, and others are part of the virtual reality console 110.

Figure 5A:
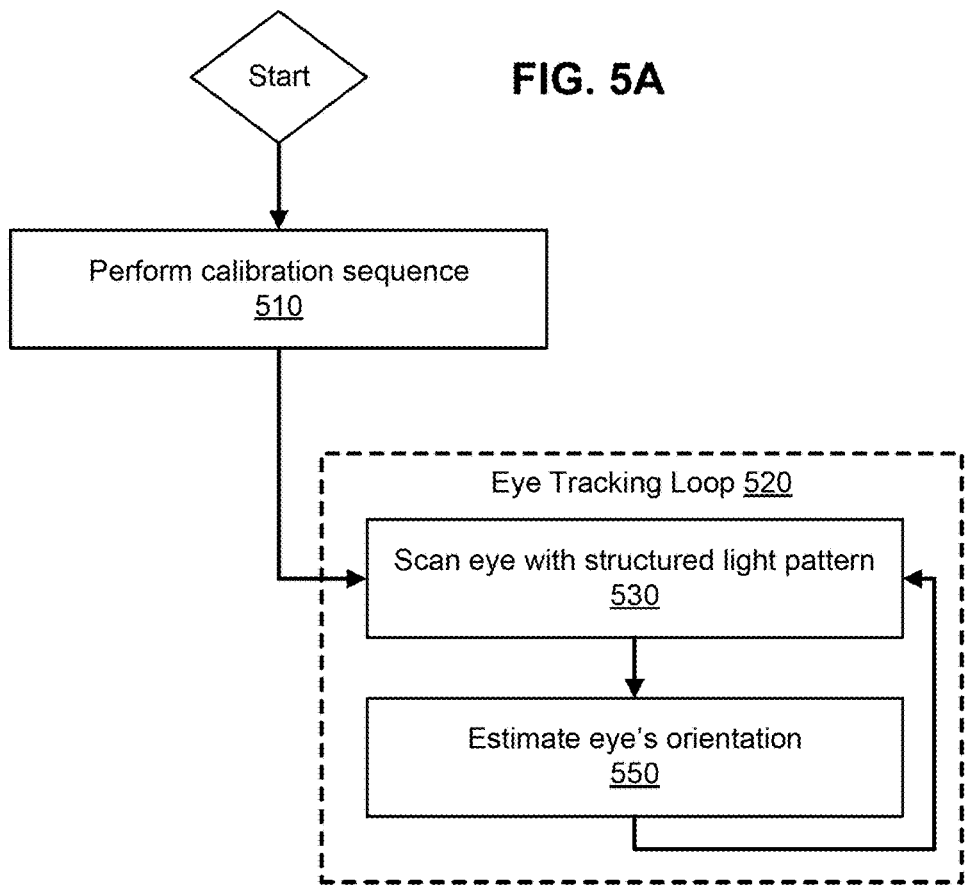
FIG. 5A is a block diagram illustrating a process for tracking eye movement, in accordance with some embodiments.

FIG. 5A is a block diagram illustrating a process for tracking eye movement, in accordance with some embodiments. The process of FIG. 5A may be performed by the eye tracking unit 400. Other entities may perform some or all of the steps of the process in other embodiments. Likewise, embodiments may include different and/or additional steps, or perform the steps in different orders.

The eye tracking unit 400 performs 510 a calibration sequence. The calibration sequence is controlled by the calibration module 420, which uses the structured light emitter 430 and the camera 440 to repeatedly scan the eye. Scanning the eye generates or trains a model of the eye, M, which is stored in the model store 410.

Next, the eye tracking unit 400 scans 530 the eye with a structured light pattern, P. Scanning 530 the eye comprises projecting a structured light pattern, P, onto the eye from the structured light emitter 310 and detecting the distorted illumination pattern projected onto a portion of the eye with a camera 320. The camera 320 captures an image, I, of the illumination pattern.

The eye's orientation is then estimated 540 by the eye orientation estimation module 460. The eye orientation estimation module 460 compares the image, I, received from scanning the eye to the model, M, stored in the model store 410. The eye orientation estimation module 460 then outputs an estimate of the orientation of the eye. The estimate of the orientation of the eye may be a pair of values, α and β, which correspond to the yaw and pitch, respectively, of the eye. After the eye's orientation is estimated 540, the eye is scanned 530 again with the structured light pattern. Thus, scanning 530 the eye and estimating 540 the eye's orientation constitute an eye tracking loop 520. Via the eye tracking loop 520, the eye's orientation can be continuously tracked.

In some embodiments, when the orientation of the eye 330 cannot be accurately estimated, the eye tracking unit 400 may output a "bad scan" error code rather than an estimate of the orientation. A "bad scan" may occur when the user blinks or due to non-idealities in the eye tracking system. A "bad scan" can be probabilistically detected by a determination that a measurement used to determine the degree to which the model of the eye, M, matches the scan of the eye (e.g., S or I) is not within a certain threshold. In some embodiments, a certain number of "bad scans" within a certain timeframe may trigger the eye tracking loop 520 to stop, and the calibration sequence may be performed 510 again.

Figure 5B:
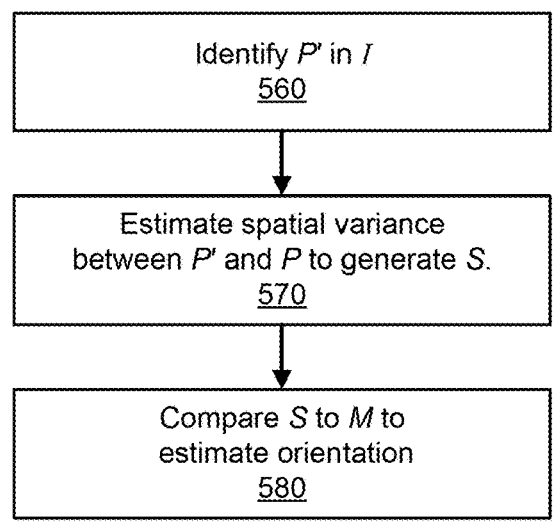
FIG. 5B is a block diagram illustrating a process for estimating the orientation of an eye in accordance with some embodiments.

FIG. 5B is a block diagram illustrating a process for estimating the orientation of an eye in accordance with some embodiments. In some embodiments, the process illustrated by FIG. 5 is part of a larger eye tracking process. For example, estimating 550 the eye's orientation as illustrated in FIG. 5A may constitute the process of FIG. 5B. The process of FIG. 5B may be performed by the eye tracking unit 400. Other entities may perform some or all of the steps of the process in other embodiments. Likewise, embodiments may include different and/or additional steps, or perform the steps in different orders.

The eye tracking unit 400 identifies a pattern, P', in an image, I. I is an image captured by a camera 440 of an illumination pattern caused by a structured light pattern, P, projected onto an eye. Identifying 560 P' in I may constitute identifying features present in the image I which correspond to features in P. For example, the eye orientation estimation module 460 may identify, through machine vision algorithms, such as edge detection algorithms, the bounds of the illumination pattern. The eye orientation estimation module 460 may also identify local maxima or local minima in the intensity of I corresponding to specific local maxima and local minima in P. The eye orientation estimation module 460 may also identify dots, lines, grids, or other features in I as corresponding to specific features in P.

Next, the spatial variance between the features of P' and P is estimated 570. Estimating 570 the spatial variance of each feature may be used to generate a surface, S, i.e., a 2D surface embedded in $\mathbb{R}^3$. The generation of S may be based on the emitter to camera geometry and the spatial variance between the features of P' and P. Techniques are known to those skilled in the art for approximating the shape of a surface based on the spatial variation between a pattern, P, emitted by a structured light emitter 430 and a identified pattern, P', based on an image, I, captured by a camera 440.

S is compared 580 to a model of the eye, M, to estimate the orientation of the eye. S may be compared 580 to M by finding the pitch and yaw angles (α and β) of the eye for which S most closely matches M. In some embodiments, comparing 580 M to S further comprises finding the value of a roll angle (γ), a translation, or some combination thereof which most closely matches M to S. In some embodiments, the spatial variance between P' and P are fit directly to the model, M. Estimating the eye's orientation may produce an estimated value of some combination of α, β, γ, and a translation vector.

Figure 6:
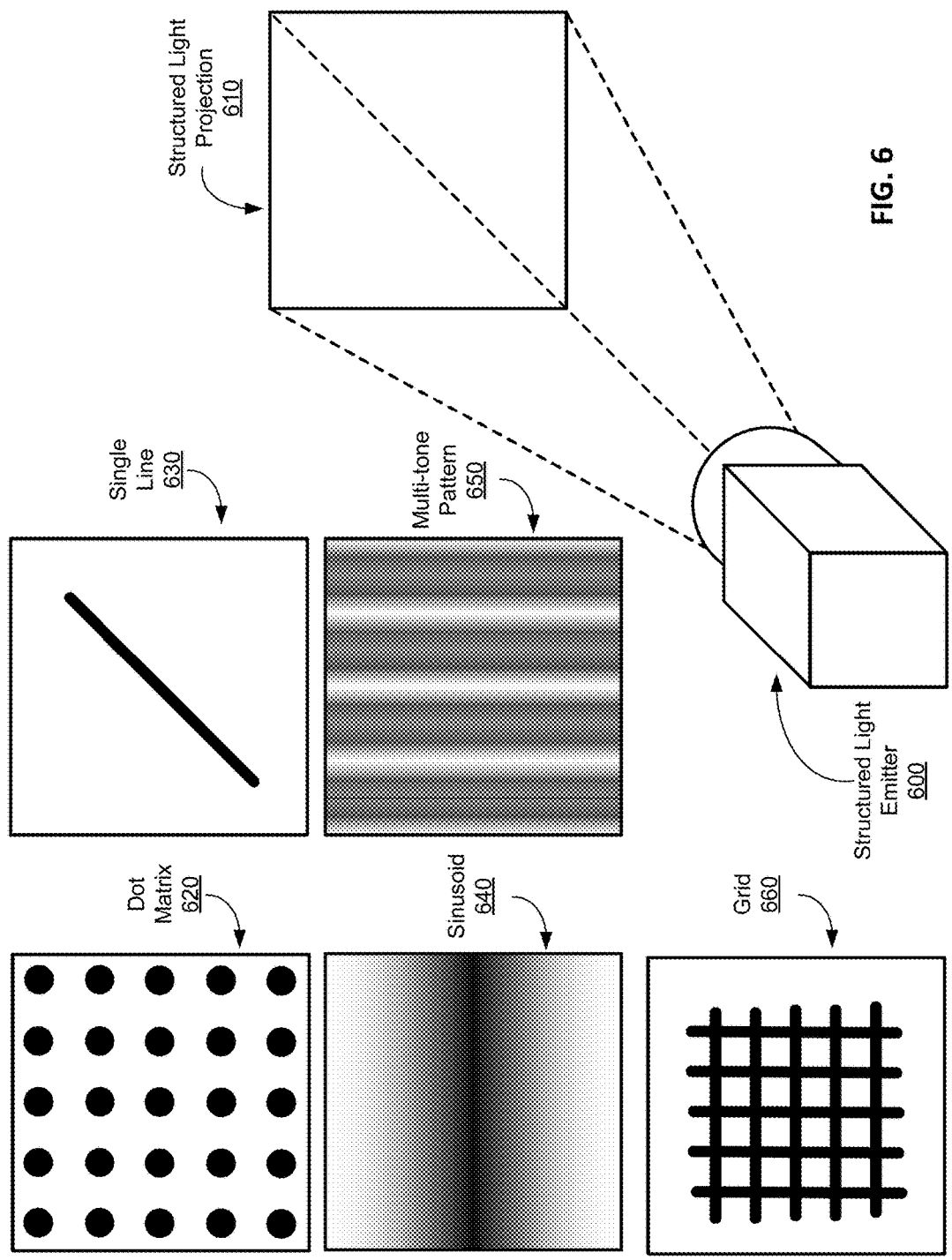
FIG. 6 is an example of an undistorted structured light projection and five example structured light patterns, in accordance with some embodiments.

FIG. 6 illustrates a structured light emitter 600 projecting structured light to form a structured light projection 610 according to an embodiment. The structured light projection 610 is shown projected on a flat surface, orthogonal to the axis of the structured light emitter 600, for the purpose of illustration. The structured light emitter 600 may be the structured light emitter 310 depicted in FIG. 3 or the structured light emitter 430 depicted in FIG. 4. FIG. 6 also shows five structured light patterns: a dot matrix 620, a single line 630, a sinusoid 640, a multi-tone pattern 650, and a grid 660. For illustrative purposes, these structured light patterns are also shown as projected upon a flat orthogonal plane. The structured light emitter 600 may output other structured light patterns as well, such as one or more bars, one or more rectangles, or pseudo-random dots.

The multi-tone pattern 650 is a combination of multiple sinusoidal patterns. The multi-tone pattern 650 in FIG. 6 depicts a structured light pattern with intensity of the form $A[\cos(\omega x)+\cos(2\omega x)]$, where x is a variable representing a position on a spatial dimension (e.g., in a Cartesian coordinate system or polar coordinate system). FIG. 6 depicts 4 periods of this function (i.e., $0<x<8\pi/\omega$), although a realized function may include a different number of periods. In some embodiments, the multi-tone pattern 650 has a period of 1 milliradian.

In general, the multi-tone pattern 650 may be a superposition of multiple sinusoidal structured light patterns which may have different wavelengths, phases, and amplitudes (e.g., $\Sigma_{i=0}^{N} A_i \cos(\omega_i x+\theta_i)$ for $A_i$, $\omega_i$, $\theta_i \in \mathbb{R}$ and $N \in \mathbb{Z}$). The sinusoidal patterns may be comprised of light of a single wavelength or a single band of wavelengths. Alternately, the sinusoidal patterns may be comprised of light of different wavelengths. The multi-tone pattern 650 may be emitted by a single structured light emitter 600 or multiple structured light emitters. It is noted that the multi-tone pattern 650 need not be horizontal as depicted in FIG. 6. In some embodiments, the multi-tone pattern 650 is an ellipsoidal pattern (e.g., $\Sigma_{i=0}^{N} A_i \cos(\sqrt{(a_i x)^2+(b_i y)^2}+\theta_i)$ for $A_i$, $a_i$, $b_i$, $\theta_i \in \mathbb{R}$ and $N \in \mathbb{Z}$ where y is a variable representing a position on a spatial dimension orthogonal to the direction to which x corresponds).

When the structured light pattern is incident on a curved surface, such as the eye, the illumination pattern may appear distorted from a perspective not on the axis of the structured light emitter 600. The eye tracking unit 400 uses the distorted light to attribute depth information to the image. In some embodiments, the structured light pattern is shifted based on the prior orientation of the eye. For example, the structured light pattern may be shifted so that the structured light pattern is centered on the position which corresponded to the border of the sclera and the cornea in the orientation of the eye detected in the previous scan. In some embodiments, when tracking fails (e.g., a "bad scan") the structured pattern of light is set to a pattern with a larger area. This may increase the probability that a portion of the cornea is illuminated by the structured light pattern. When the eye's orientation is detected again, the structured light pattern can be reset to a pattern with a smaller area.

Additional Configuration Information

The foregoing description of the embodiments of the disclosure has been presented for the purpose of illustration; it is not intended to be exhaustive or to limit the embodiments to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the disclosure may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the disclosure may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the embodiments be limited not by this detailed description, but rather by any claims that issue on an application based hereon. Accordingly, the disclosure of the embodiments is intended to be illustrative, but not limiting, of the scope of the detailed description, which is set forth in the following claims.

What is claimed is:

1. An eye tracking unit comprising:
   a structured light emitter configured to illuminate an eye of a user with a structured light pattern, the structured light pattern producing an illumination pattern on a portion of a surface of the eye;
   a camera configured to capture an image of the illumination pattern on the portion of the surface of the eye; and
   an eye orientation estimation module configured to estimate a foveal axis of the eye based on the image captured by the camera and a model of the eye, the foveal axis defining an orientation of the eye.

2. The eye tracking unit of claim 1, wherein the eye tracking unit is a component of a head-mounted display (HMD), the HMD comprising:
   a display element configured to display content to a user wearing the HMD; and
   an optics block configured to direct light from the display element to an exit pupil of the HMD.

3. The eye tracking unit of claim 1, further comprising a calibration module configured to:
   control a display element to display a visual indicator at a position on the display element;
   receive, from the camera, a second image of a second illumination pattern on the portion of the surface of the eye; and
   train the model of the eye of the user based on the captured second image and based on the position of the visual indicator.

4. The eye tracking unit of claim 1, wherein the eye orientation estimation module is configured to:
   estimate a direction of a pupillary axis of the eye using the captured image; and
   estimate the foveal axis of the eye based on the estimated direction of the pupillary axis and based on an offset between the pupillary axis and the foveal axis.

5. The eye tracking unit of claim 1, wherein the eye orientation estimation module is configured to:
   determine a shape of the portion of the surface of the eye based on distortion in the illumination pattern captured in the image; and
   compare the model of the eye to the determined shape of the portion of the surface of the eye.

6. The eye tracking unit of claim 1, wherein the eye orientation estimation module is configured to:
   detect positions for each of a plurality of illumination points in the captured image of the illumination pattern;
   determine a three-dimensional position of each illumination point based on a comparison of the position of the illumination point in the captured image of the illumination pattern to a corresponding angle from the structured light emitter of the illumination point in the structured light pattern; and
   compare the model of the eye to the determined 3-dimensional positions of the illumination points.

7. The eye tracking unit of claim 1, wherein the eye orientation estimation module is configured to estimate the foveal axis of the eye based in part on a position of a feature of the eye based on the captured image and the model of the eye, the feature selected from a group consisting of the curvature of the cornea, the cornea-sclera interface, iris features beneath the cornea, and the vertex of the cornea.

8. The eye tracking unit of claim 1, wherein the eye orientation estimation module is configured to estimate the foveal axis of the eye based in part on determining a yaw, pitch, and roll rotation for the eye and a 3-dimensional translation vector for the eye.

9. The eye tracking unit of claim 1, wherein the structured light pattern is selected from a group consisting of a dot matrix, a sinusoid, single or multiple line segments, and a multi-tone pattern.

10. An eye tracking unit comprising:
a first structured light emitter configured to illuminate a first eye of a user with a first structured light pattern, wherein the first structured light pattern produces a first illumination pattern on a portion of a surface of the first eye;
a second structured light emitter configured to illuminate a second eye of the user with a second structured light pattern, wherein the second structured light pattern produces a second illumination pattern on a portion of a surface of the second eye;
a first camera configured to capture a first image of the first illumination pattern on the portion of the surface of the first eye;
a second camera configured to capture a second image of the second illumination pattern on the portion of the surface of the second eye; and
an eye orientation estimation module configured to:
estimate a first foveal axis of the first eye based on the first image captured by the first camera and a model, the first foveal axis defining an orientation of the first eye, and
estimate a second foveal axis of the second eye based on the second image captured by the second camera and the model, the second foveal axis defining an orientation of the second eye.

11. The eye tracking unit of claim 10, wherein the eye tracking unit is a component of a head-mounted display (HMD), the HMD configured to determine an inter-pupillary distance of the user using the first foveal axis and the second foveal axis.

12. The eye tracking unit of claim 10, wherein the eye orientation estimation module is configured to:
estimate a direction of a first pupillary axis of the first eye using the first captured image; and
estimate the first foveal axis of the first eye based on the estimated direction of the first pupillary axis and based on an offset between the first pupillary axis and the first foveal axis.

13. The eye tracking unit of claim 10, wherein the eye orientation estimation module is configured to:
detect positions for each of a plurality of illumination points in the first captured image of the first illumination pattern;
determine a three-dimensional position of each illumination point based in part on comparing the position of the illumination point in the first captured image of the illumination pattern to a corresponding angle from the first structured light emitter of the illumination point in the first structured light pattern; and
compare the model to the determined three-dimensional positions of the illumination points.

14. The eye tracking unit of claim 10, wherein the eye orientation estimation module is configured to estimate the first foveal axis and the second foveal axis based in part on determining, for each of the first eye and the second eye, a respective yaw, pitch, and roll rotation and a respective translation vector for the eye.

15. A method comprising:
projecting a structured light pattern onto an eye of a user, the structured light pattern producing an illumination pattern on a portion of a surface of the eye;
capturing an image of the illumination pattern on the portion of the surface of the eye; and
estimating a foveal axis of the eye based on the captured image and a model of the eye, the foveal axis defining an orientation of the eye.

16. The method of claim 15, further comprising:
controlling a display element to display a visual indicator at a position on the display element;
capturing a second image of a second illumination pattern on a portion of a surface of the eye; and
training the model of the eye of the user based on the captured second image and based on the position of the visual indicator.

17. The method of claim 15, wherein estimating the foveal axis of the eye comprises:
estimating a direction of a pupillary axis of the eye using the captured image; and
estimating the foveal axis of the eye based on the estimated direction of the pupillary axis and based on an offset between the pupillary axis and the foveal axis.

18. The method of claim 15, wherein estimating the foveal axis of the eye comprises:
determining a shape of the portion of the surface of the eye based on distortion in the illumination pattern in the captured image; and
comparing the model of the eye to the determined shape of the portion of the surface of the eye.

19. The method of claim 15, wherein estimating the foveal axis of the eye comprises:
detecting positions for each of a plurality of illumination points in the captured image of the illumination pattern;
determining a three-dimensional position of each illumination point based on a comparison of a position of the illumination point in the captured image of the illumination pattern to a corresponding angle from an emitter of the illumination point in the structured light pattern; and
comparing the model of the eye to the determined three-dimensional positions of the illumination points.

20. The method of claim 15, wherein the foveal axis of the eye is estimated based in part on determining a yaw, pitch, and roll rotation for the eye and a three-dimensional translation vector for the eye.

* * * * *